(12) United States Patent
Yanagisawa

(10) Patent No.: US 7,923,091 B2
(45) Date of Patent: Apr. 12, 2011

(54) INDOLE COMPOUND, OPTICAL FILTER AND OPTICAL RECORDING MATERIAL

(75) Inventor: Satoshi Yanagisawa, Tokyo (JP)

(73) Assignee: Adeka Corporation, Tokyo (JP)

( * ) Notice: Subject to any disclaimer, the term of this patent is extended or adjusted under 35 U.S.C. 154(b) by 500 days.

(21) Appl. No.: 11/996,502

(22) PCT Filed: Jul. 19, 2006

(86) PCT No.: PCT/JP2006/314229
§ 371 (c)(1),
(2), (4) Date: Jan. 23, 2008

(87) PCT Pub. No.: WO2007/018015
PCT Pub. Date: Feb. 15, 2007

(65) Prior Publication Data
US 2009/0092782 A1     Apr. 9, 2009

(30) Foreign Application Priority Data

Aug. 11, 2005 (JP) ................................. 2005-233329

(51) Int. Cl.
*B32B 3/02* (2006.01)
*G11B 7/246* (2006.01)
(52) U.S. Cl. .............. 428/64.8; 430/270.15; G9B/7.148
(58) Field of Classification Search ................. 428/64.4, 428/64.8; 430/270.15, 270.18; G9B/7.148
See application file for complete search history.

(56) References Cited

U.S. PATENT DOCUMENTS

| 6,558,768 B2 | 5/2003 | Noguchi et al. |
| 6,815,031 B2 | 11/2004 | Huang et al. |
| 2004/0126702 A1 | 7/2004 | Mikoshiba |

FOREIGN PATENT DOCUMENTS

| JP | 2002-234259 A | 8/2002 |
| JP | 2003-237233 A | 8/2003 |
| JP | 2003-313447 A | 11/2003 |
| JP | 2004-58365 | 2/2004 |
| JP | 2004-102223 A | 4/2004 |
| JP | 2004-174838 | 6/2004 |
| JP | 2004-209771 A | 7/2004 |

OTHER PUBLICATIONS

STN search history for compounds of general formula (I) from Aug. 14, 2010.*
Timokhina et al., "Mesomerically stabilized thioaldehydes. 3-Thioformylindole and its alkyl (phenyl) derivatives," Khimiya Geterotsiklicheskikh Soedinenii, No. 4, pp. 493-496 (1996).
Blunt et al., "Syntheses of Haptens Related to the Benzenoid and Indole Portions of Sporidesmin A; $^{13}$ C N.M.R. Spectra of Indole Derivatives," Aust. J. Chem., vol. 32, No. 5, pp. 1045-1054 (1979).
Genikina, "Kinetics of hydrolysis of 3-indolylmethylindenedimethylimmonium fluoroborate in a phosphate buffer," Chem. Abs., vol. 104, p. 480, 5282u (Compound I) (1986).
Babievskii, "Reaction of nitro compounds with immonium salts 1. Nitrovinylation of indoles," Izvestiya Akademii Nauk SSSR, Seiya Khimicheskaya, No. 10, pp. 2310-2313 (1977).
Kobayashi, "Azafulvenes 2. Formation of Iminium Salt from Pyrrole- and Indolecarbaldehyde and Its Reaction with Bases," Bulletin of Chem. Soc. of Japan, vol. 48, No. 11, pp. 3255-3258 (1975).
Chinese Official Action—200680029239.5—Oct. 9, 2010.
Blunt, J.W.; "Syntheses of Haptens Related to the Benzenoid and Indole Portions of Sporidesmin A; Carbon-13 NMR Spectra of Indole Derivates"—Australian Journal of Chemistry, vol. 32, No. 5, pp. 1045-1054, Dec. 31, 1979.

* cited by examiner

*Primary Examiner* — Mark Ruthkosky
*Assistant Examiner* — Gerard T Higgins
(74) *Attorney, Agent, or Firm* — Young & Thompson

(57) ABSTRACT

An indole compound represented by general formula (I):

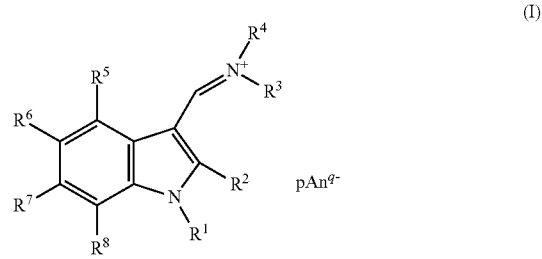

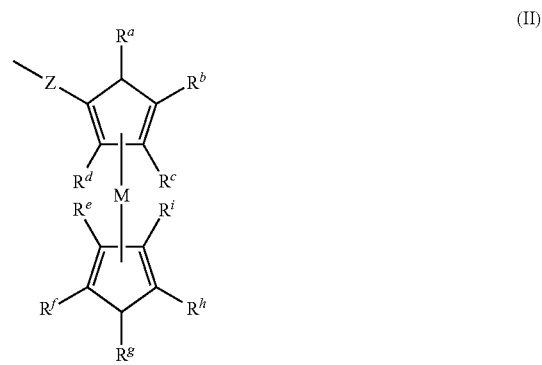

wherein $R^1$ and $R^2$ each represent a hydrogen atom, a hydrocarbon group having 1 to 30 carbon atoms or a substituent represented by general formula (II); $R^3$ and $R^4$ each represent an alkyl group having 1 to 10 carbon atoms, an alkoxy group having 1 to 10 carbon atoms or an aryl group having 6 to 30 carbon atoms; $R^5$, $R^6$, R7, and $R^8$ each represent a hydrogen atom, a hydrocarbon group having 1 to 30 carbon atoms, a halogen atom, a hydroxyl group, a nitro group, a cyano group, NHR or NR'R"; R, R', and R" each represent an alkyl group having 1 to 10 carbon atoms, or R' and R" are taken together to form a ring; $R^5$ and $R^6$, $R^6$ and $R^7$, or $R^7$ and $R^8$ may be taken together to form a ring; $An^{q-}$ represents a q-valent anion; q represents 1 or 2; and p represents a coefficient necessary to maintain charge neutrality.

5 Claims, No Drawings

INDOLE COMPOUND, OPTICAL FILTER AND OPTICAL RECORDING MATERIAL

TECHNICAL FIELD

This invention relates to a novel indole compound, an optical filter, and an optical recording medium. The indole compound is useful as an optical element and the like. The indole compound is particularly useful as an ultraviolet (UV) absorber incorporated into an optical filter for application to image displays. It is also useful as an optical recording material for use in optical recording media capable of high density optical writing and reading with low energy lasers having wavelengths in the visible to near infrared regions.

BACKGROUND ART

Optical recording media have been widespread generally because of their superiority such as high recording capacity and non-contact write/read system. Recordable optical disks such as WORMs, CD-Rs, and DVD-Rs record information by irradiating a very small area of the optical recording layer with a focused laser beam to change the properties of the irradiated area and reproduce the recorded information making use of the difference in reflected light quantity between the recorded area and the non-recorded area.

Wavelengths of semiconductor lasers used in writing and reading information on the currently available optical disks of the type described are in the ranges of 750 to 830 nm for CD-Rs and of 620 to 690 nm for DVD-Rs. In pursuit of a further increased capacity, optical disks using shorter wavelength lasers have been under study. For example, those using a write wavelength of 380 to 420 nm have been studied.

Various kinds of compounds are used to form an optical recording layer of optical recording media for short wavelength lasers. For example, Patent Document 1 reports azo compounds; Patent Document 2, porphyrin compounds; Patent Document 3, triazole compound metal complexes. These compounds, however, are not always good for use as an optical recording material forming an optical recording layer in view of their absorption wavelength characteristics.

On the other hand, compounds that absorb light of 300 to 390 nm wavelength are used as a UV absorber of an optical filter for application to image display devices including liquid crystal displays (LCDs), plasma display panels (PDPs), electroluminescence displays (ELDs), cathode ray tubes (CRTs), fluorescent display tubes, and field emission displays (FEDs).

For example, Patent Document 4 discloses a filter for organic electroluminescence (EL) displays that contains a UV absorber and blocks light of 200 to 410 nm wavelength. However, the UV absorber used in the filter for organic EL displays is not always suited for use as a UV absorber of optical filters in view of its absorption wavelength characteristic.

Patent Document 1: JP 2004-209771A
Patent Document 2: JP 2004-58365A
Patent Document 3: JP 2004-174838A
Patent Document 4: JP 2004-102223A

DISCLOSURE OF THE INVENTION

Problem to be Solved by the Invention

An object of the present invention is to provide a compound having optical characteristics suitable for use as an optical element particularly of an optical filter for image display devices and of an optical recording material for optical recording media writable or readable with short wavelength laser light.

Means for Solving the Problem

As a result of extensive investigations, the present inventors have found that a specific indole compound having an imino structure has absorption wavelength characteristics meeting the requirements of an optical element for the above applications and thus reached the invention.

The present invention provides an indole compound represented by general formula (I) shown below, an optical filter containing the indole compound, and an optical recording material containing the indole compound. The optical recording material is useful to form an optical recording layer on a substrate to provide an optical recording medium.

[Chemical Formula 1]

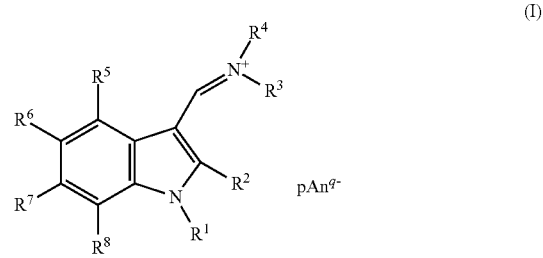

(I)

Wherein $R^1$ and $R^2$ each represent a hydrogen atom, a hydrocarbon group having 1 to 30 carbon atoms or a substituent represented by general formula (II) below; $R^3$ and $R^4$ each represent an alkyl group having 1 to 10 carbon atoms, an alkoxy group having 1 to 10 carbon atoms or an aryl group having 6 to 30 carbon atoms; $R^5$, $R^6$, $R^7$, and $R^8$ each represent a hydrogen atom, a hydrocarbon group having 1 to 30 carbon atoms, a halogen atom, a hydroxyl group, a nitro group, a cyano group, NHR or NR'R"; R, R', and R" each represent an alkyl group having 1 to 10 carbon atoms, or R' and R" are taken together to form a ring; or $R^5$ and $R^6$, or $R^6$ and $R^7$, or $R^7$ and $R^8$ may be taken together to form a ring; $An^{q-}$ represents a q-valent anion; q represents 1 or 2; and p represents a coefficient necessary to maintain charge neutrality.

[Chemical Formula 2]

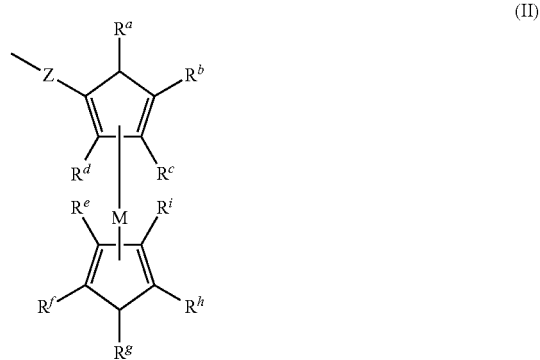

(II)

Wherein $R^a$, $R^b$, $R^c$, $R^d$, $R^e$, $R^f$, $R^g$, $R^h$, and $R^i$ each represent a hydrogen atom or an alkyl group having 1 to 4 carbon atoms, wherein a methylene group of the alkyl group may be replaced by —O— or —CO—; Z represents a single bond or a substituted or unsubstituted alkylene group having 1 to 8 carbon atoms, wherein a methylene group of the alkylene group may be replaced by —O—, —S—, —CO—, —COO—, —OCO—, —SO$_2$—, —NH—, —CONH—, —NHCO—, —N=CH— or —CH=CH—; and M represents a metal atom.

BEST MODE FOR CARRYING OUT THE INVENTION

The indole compound and the optical filter and optical recording material containing the indole compound will be described in detail with reference to their preferred embodiments.

The indole compound of the invention is described first.

In general formula (I), examples of the hydrocarbon group having 1 to 30 carbon atoms represented by $R^1$, $R^2$, $R^5$, $R^6$, $R^7$, and $R^8$ include alkyl groups, such as methyl, ethyl, propyl, isopropyl, butyl, sec-butyl, tert-butyl, isobutyl, amyl, isoamyl, tert-amyl, hexyl, cyclohexyl, cyclohexylmethyl, 2-cyclohexylethyl, heptyl, isoheptyl, tert-heptyl, n-octyl, isooctyl, tert-octyl, 2-ethylhexyl, nonyl, isononyl, decyl, dodecyl, tridecyl, tetradecyl, pentadecyl, hexadecyl, heptadecyl, and octadecyl; alkenyl groups, such as vinyl, 1-methylethenyl, 2-methylethenyl, propenyl, butenyl, isobutenyl, pentenyl, hexenyl, heptenyl, octenyl, decenyl, pentadecenyl, and 1-phenylpropen-3-yl; phenyl; naphthyl; alkylaryl groups, such as 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 4-octylphenyl, 4-(2-ethylhexyl)phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-t-butylpheyl, and cyclohexylphenyl; arylalkyl groups, such as benzyl, phenethyl, 2-phenylpropan-2-yl, diphenylmethyl, triphenylmethyl, styryl, and cinnamyl; and the above recited hydrocarbon groups interrupted by an ether and/or a thioether linkage, such as 2-methoxyethyl, 3-methoxypropyl, 4-methoxybutyl, 2-butoxyethyl, methoxyethoxyethyl, methoxyethoxyethoxyethyl, 3-methoxybutyl, 2-phenoxyethyl, 3-phenoxypropyol, 2-methylthioethyl, and 2-phenylthioethyl. These hydrocarbon groups may be substituted, e.g., with an alkoxy group, an alkenyl group, a nitro group, a cyano group, or a halogen group. When the hydrocarbon group is substituted with one or more groups selected from alkoxy groups, alkenyl groups, and a cyano group, the total carbon atom number of the hydrocarbon group inclusive of the substituent(s) is 30 at the most.

Examples of the alkyl group having 1 to 10 carbon atoms represented by $R^3$, $R^4$, R, R', and R" include methyl, ethyl, propyl, isopropyl, butyl, sec-butyl, tert-butyl, isobutyl, amyl, isoamyl, tert-amyl, hexyl, cyclohexyl, heptyl, isoheptyl, tertheptyl, n-octyl, isooctyl, tert-octyl, 2-ethylhexyl, nonyl, and decyl. Examples of the alkoxy group having 1 to 10 carbon atoms are methoxy, ethoxy, isopropoxy, propoxy, butoxy, pentoxy, isopentyloxy, hexyloxy, heptyloxy, octyloxy, and 2-ethylhexyloxy. Examples of the aryl group having 6 to 30 carbon atoms are phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 4-octylphenyl, 4-(2-ethylhexyl)phenyl, 4-stearylphenyl, 2,3-dimethyhlphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, 2,5-di-tert-butylphenyl, 2,6-di-tert-butylphenyl, 2,4-di-tert-pentylphenyl, 2,5-di-tert-amylphenyl, 2,5-di-tert-octylphenyl, 2,4-dicumylphenyl, cyclohexylphenyl, biphenyl, 2,4,5-trimethylphenyl, benzyl, phenethyl, 2-phenylpropan-2-yl, diphenylmethyl, triphenylmethyl, styryl, and cinnamyl.

Examples of the halogen atom represented by $R^5$, $R^6$, $R^7$, and $R^8$ in general formula (I) are fluorine, chlorine, bromine, and iodine.

Examples of the ring formed by R' and R" taken together in general formula (I) include a piperidine, a piperazine, a pyrrolidine, and a morpholine ring. Examples of the ring formed by a combination of $R^5$ and $R^6$, a combination of $R^6$ and $R^7$, or a combination of $R^7$ and $R^8$ are a cyclobutene, a cyclopentene, a cyclohexene, a benzene, and a pyridine ring.

Examples of the alkyl group having 1 to 4 carbon atoms represented by $R^a$, $R^b$, $R^c$, $R^d$, $R^e$, $R^f$, $R^g$, $R^h$, and $R^i$ in general formula (II) include methyl, ethyl, propyl, isopropyl, butyl, sec-butyl, tert-butyl, isobutyl, methoxy, ethoxy, propoxy, isopropoxy, methoxymethyl, ethoxymethyl, 2-methoxyethyl, acetyl, 1-carbonylethyl, acetylmethyl, 1-carbonylpropyl, 2-oxobutyl, 2-acetylethyl, and 1-carbonylisopropyl. Examples of the substituted or unsubstituted alkylene group having 1 to 8 carbon atoms include methylene, ethylene, propylene, methylethylene, butylene, 1-methylpropylene, 2-methylpropylene, 1,2-dimethylpropylene, 1,3-dimethylpropylene, 1-methylbutylene, 2-methylbutylene, 3-methylbutylene, 4-methylbutylene, 2,4-dimethylbutylene, 1,3-dimethylbutylene, pentylene, hexylene, heptylene, octylene, ethane-1,1-diyl, propane-2,2-diyl, ethenylene, propenylene, methyleneoxy, ethyleneoxy, oxymethylene, thiomethylene, carbonylmethylene, carbonyloxymethylene, methylenecarbonyloxy, sulfonylmethylene, aminomethylene, acetylamino, ethylenecarboxyamide, and ethaneimidoyl. Examples of the metal atom represented by M include iron, cobalt, nickel, copper, zinc, aluminum, titanium, zirconium, vanadium, niobium, tantalum, chromium, molybdenum, tungsten, osmium, manganese, ruthenium, gallium, indium, silicon, germanium, tin, antimony, bismuth, gold, silver, palladium, rhodium, platinum, iridium, yttrium, lanthanum, praseodymium, neodymium, promethium, gadolinium, dysprosium, holmium, lutetium, and scandium.

The anion represented by $An^{q-}$ in general formula (I) includes monovalent ones and divalent ones. Examples of the monovalent anions include halide ions, e.g., a chloride, a bromide, an iodide, and a fluoride ion; inorganic anions, e.g., a perchlorate, a chlorate, a thiocyanate, a hexafluorophosphate, a hexafluoroantimonate, and a tetrafluoroborate anion; organic sulfonate anions, e.g., a benzenesulfonate, a toluenesulfonate, a trifluoromethanesulfonate, a diphenylamine-4-sulfonate, 2-amino-4-methyl-5-chlorobenzenesulfonate, and a 2-amino-5-nitrobenzenesulfonate anion; organic phosphate anions, e.g., an octylphosphate, a dodecylphosphate, an octadecylphosphate, a phenylphosphate, a nonylphenylphosphate, and a 2,2'-methylenebis(4,6-di-tert-butylphenyl)phosphonate anion; a bis(trifluoromethyl-sulfonyl)imide anion, a bis(perfluorobutanesulfonyl)imide anion, a perfluoro-4-ethylcyclohexanesulfonate anion, a tetrakis(pentafluorophenyl) borate anion, and a tris(fluoroalkylsulfonyl)carbanion. Examples of the divalent anions include a benzenesulfonate and a naphthalenedisulfonate anion. If desired, a quencher anion capable of deexciting (quenching) an active molecule in an excited state, a metallocene compound anion of, for example, a ferrocene or a ruthenocene compound having an anionic group (e.g., carboxyl, phosphonic or sulfonic group) on the cyclopentadienyl ring, and the like can be used.

Examples of the quencher anion include anions represented by general formulae (A), (B), and (C) shown below and those described in JP 60-234892A, JP 5-43814A, JP 5-305770A, JP 6-239028A, JP 9-309886A, JP 9-323478, JP 10-45767A, JP 11-208118A, JP 2000-168237A, JP 2002-201373A, JP 2002-206061A, JP 2005-297407A, JP 7-96334B, and WO98/29257.

[Chemical Formula 3]

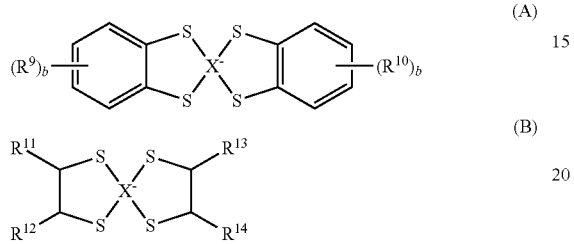

(A)

(B)

wherein X represents a nickel atom or a copper atom; $R^9$ and $R^{10}$ each represent a halogen atom, an alkyl group having 1 to 8 carbon atoms, an aryl group having 6 to 30 carbon atoms, or —$SO_2$-G; G represents an alkyl group, an aryl group, a halogen-substituted aryl group, a dialkylamino group, a diarylamino group, a piperidino group or a morpholino group; a and b each represent an integer of 0 to 4; and $R^{11}$, $R^{12}$, $R^{13}$, and $R^{14}$ each represent an alkyl group, an alkylphenyl group, an alkoxyphenyl group or a halogen-substituted phenyl group.

[Chemical Formula 4]

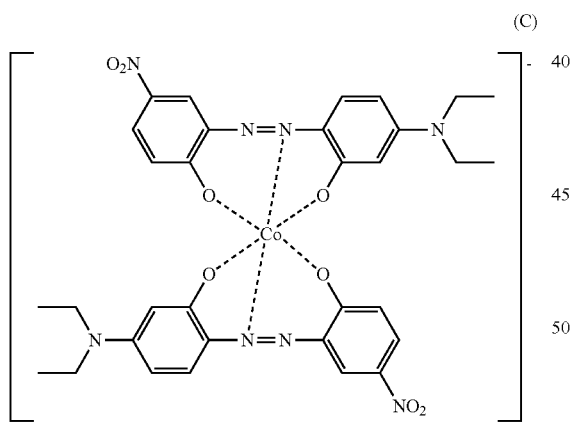

(C)

Of the indole compounds of the invention preferred are those in which $R^1$ is a hydrocarbon group having 1 to 30 carbon atoms, particularly an alkyl group having 1 to 8 carbon atoms or an aryl group having 6 to 13 carbon atoms; $R^2$ is a hydrogen atom or a hydrocarbon group having 1 to 30 carbon atoms, particularly a hydrogen atom, an alkyl group having 1 to 8 carbon atoms or an aryl group having 6 to 13 carbon atoms; $R^3$ is an alkyl group having 1 to 10 carbon atoms, particularly an alkyl group having 1 to 4 carbon atoms; and $R^4$ is an alkyl group having 1 to 10 carbon atoms, particularly an alkyl group having 1 to 4 carbon atoms, in view of the cost and optical characteristics.

Compound Nos. 1 to 24 shown below are specific examples of the indole compounds according to the invention.

[Chemical Formula 5]

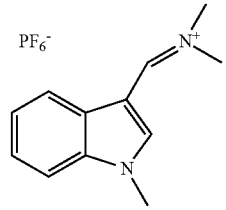

Compound No. 1

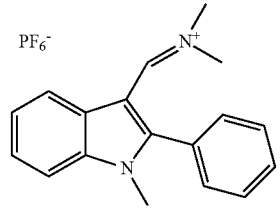

Compound No. 2

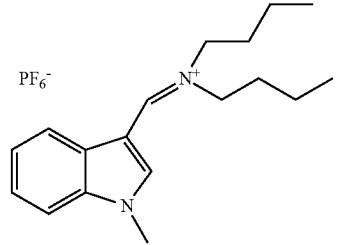

Compound No. 3

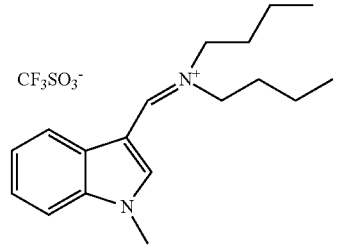

Compound No. 4

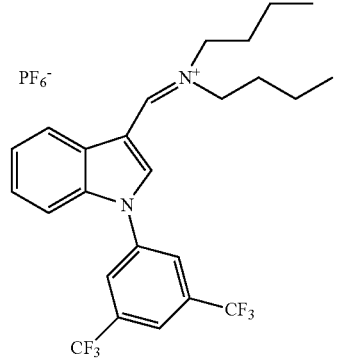

Compound No. 5

Compound No. 6
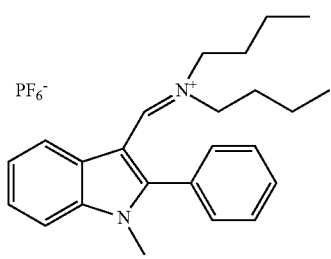
Compound No. 7
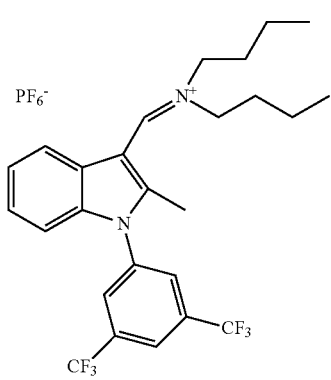
Compound No. 8
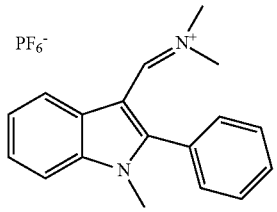
Compound No. 9
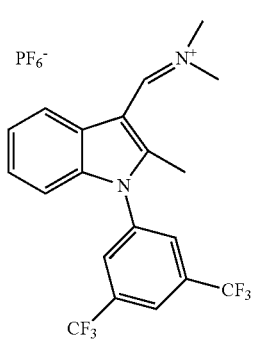
Compound No. 10
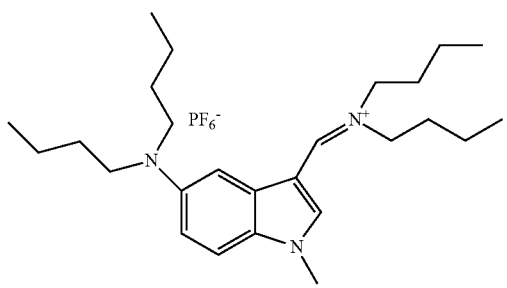
Compound No. 11
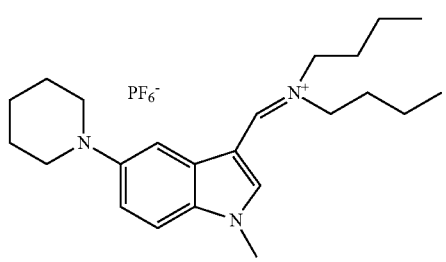
[Chemical Formula 6]
Compound No. 12
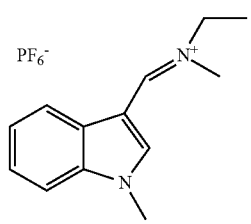
Compound No. 13
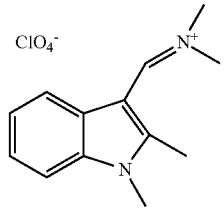
Compound No. 14
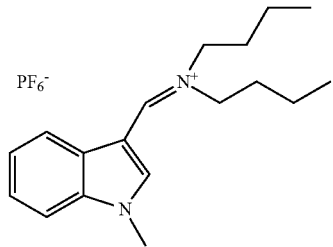
Compound No. 15
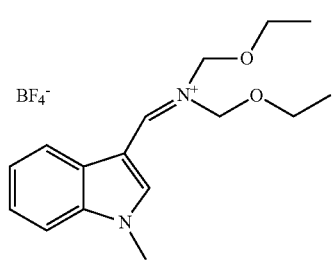

Compound No. 16
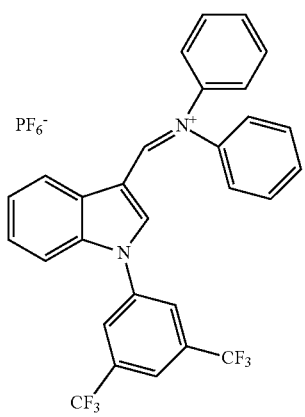
Compound No. 17
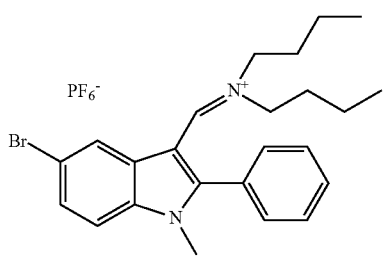
Compound No. 18
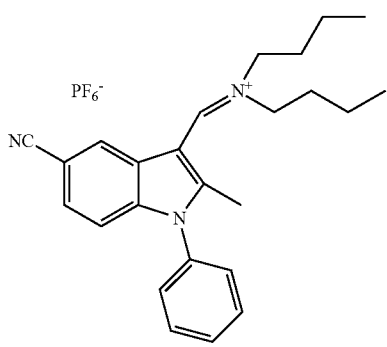
Compound No. 19
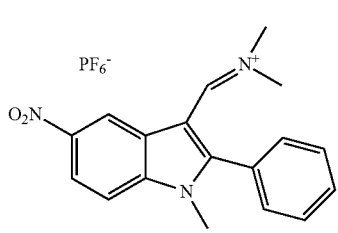
Compound No. 20
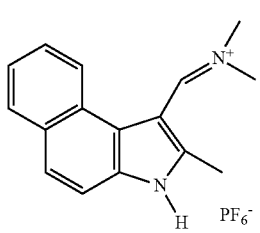
Compound No. 21
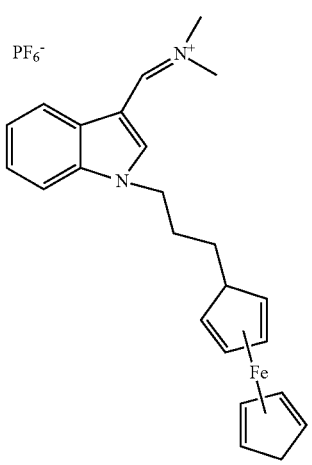
Compound No. 22
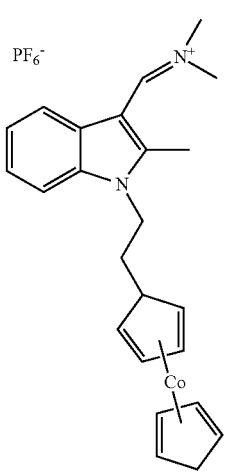
[Chemical Formula 7]
Compound No. 23
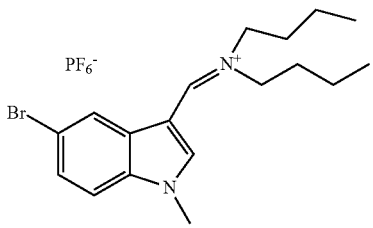
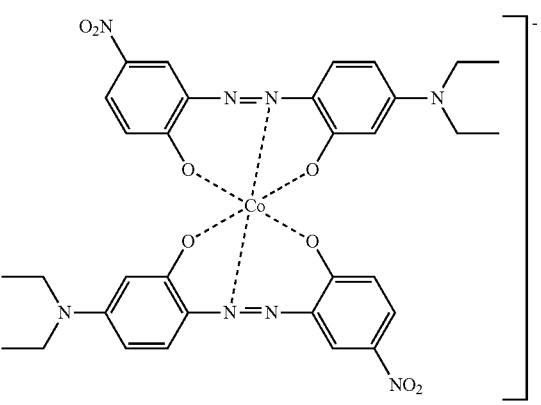

-continued

Compound No. 24

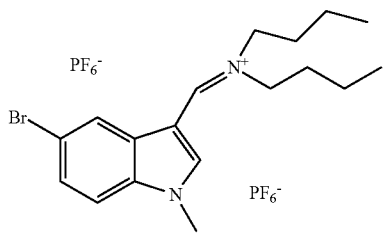

The indole compound of the invention represented by general formula (I) is not restricted by the process of preparation and can be obtained through well-known, ordinary reactions. For instance, the indole compound having a monovalent anion is synthesized through the following route:

[Chemical Formula 8]

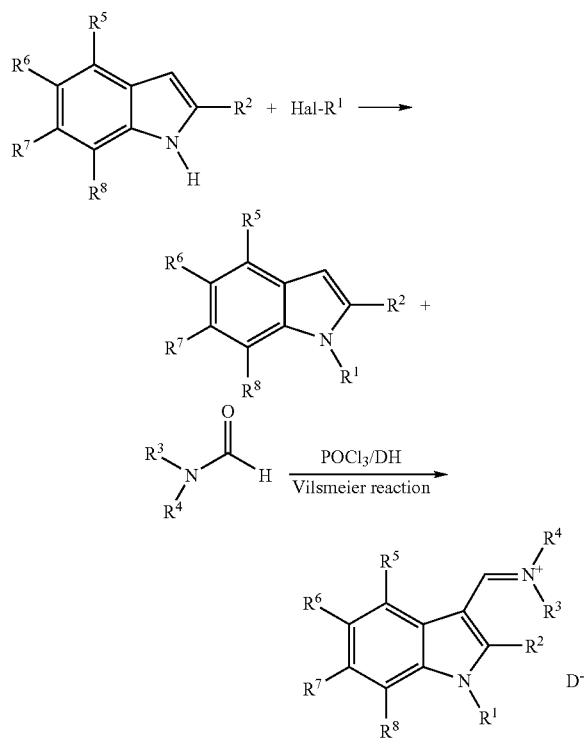

wherein $R^1$, $R^2$, $R^3$, $R^4$, $R^5$, $R^6$, $R^7$, $R^8$ are as defined above; Hal represents a halogen atom; and $D^-$ represents an anion.

The indole compound of the invention is useful as an optical element that absorbs light of specific wavelengths, particularly 320 to 420 nm, to perform its function. Examples of such an optical element include a UV absorber incorporated into optical filters and an optical recording agent used to form an optical recording layer of an optical recording medium such as an optical disk.

The indole compound of the invention also finds use as an intermediate of pharmaceuticals, agricultural chemicals, perfumes, dyes, and so forth and in various functional materials.

The optical filter according to the present invention is then described.

The optical filter according to the invention contains the indole compound of the invention. The indole compound has an absorption maximum in the wavelength range of 340 to 390 nm and absorbs and blocks light of 410 nm and shorter wavelengths, i.e., UV light and part of visible light. Therefore, the optical filter containing the indole compound is especially suited for application to image displays as an optical filter used to improve display qualities. The optical filter of the invention is useful for application to not only image displays but analysis equipment, fabrication of semiconductor devices, astronomical observation, optical communications, and spectacle lenses, and the like.

The optical filter of the invention is usually disposed in front of a display device. The optical filter may be affixed directly to the front surface of a display device or to the front or the back side of a front plate if provided in front of a display device.

The optical filter typically comprises a transparent substrate and a primer layer, an antireflection layer, a hard coat layer, a lubricating layer, etc. formed on the transparent substrate according to necessity. The indole compound of the invention and other optional components, such as a color compound other than the indole compound of the invention and various stabilizers, are incorporated into the optical filter by, for example, (1) incorporating into the transparent substrate or any selected layer(s), (2) coating to the transparent substrate or any selected layer(s), (3) incorporating into an adhesive applied between adjacent two selected from the transparent substrate and the layers, or (4) incorporating into an independently provided light absorbing layer.

The indole compound is used in the optical filter usually in an amount of 1 to 1000 mg/m$^2$, preferably 5 to 100 mg/m$^2$, per unit area of the optical filter. Amounts less than 1 mg/m$^2$ may fail to produce sufficient effects of light absorption. Amounts exceeding 1000 mg/m$^2$ may result in noticeable coloring of the filter, which can impair display quality or reduce the display brightness.

In making the optical filter containing the indole compound in, for example, a pressure-sensitive adhesive layer, the above recited per-unit-area amount of the indole compound is achieved usually by adding the indole compound preferably in an amount of 0.001 to 0.05 parts by mass and a solvent (e.g., methyl ethyl ketone) preferably in an amount of 40 to 500 parts by mass to 100 parts by mass of an adhesive (e.g., an acrylic adhesive) to prepare a vanish, applying the varnish to a transparent substrate (e.g., a PET film) having been subjected to adhesion enhancement treatment, and curing the adhesive to provide an optical filter having a pressure-sensitive adhesive layer (cured film) with a thickness of 0.1 to 10 μm.

Whichever of the aforementioned methods (1) to (4) may be adopted to incorporate the indole compound and other optional components into the optical filter of the invention, the compounding ratio of the components may be decided according to the above example.

The transparent substrate can be of inorganic materials such as glass and polymeric materials. Examples of polymeric materials include cellulose esters, such as diacetyl cellulose, triacetyl cellulose (TAC), propionyl cellulose, butyryl cellulose, acetylpropionyl cellulose, and nitrocellulose; polyamides; polycarbonates; polyesters, such as polyethylene terephthalate, polyethylene naphthalate, polybutylene terephthalate, poly(1,4-cyclohexane dimethylene terephthalate), and poly(ethylene-1,2-diphenoxyethane-4,4'-dicarboxylate); polystyrenes; polyolefins, such as polyethylene, polypropylene, and polymethylpentene; acrylic resins, such as polymethyl methacrylate; polysulfones; polyether sulfones; polyether ketones; polyether imides; polyoxyethylenes; and norbornene resins. It is preferred for the transparent substrate to have a transmittance of at least 80%, still preferably 86% or higher; a haze of not more than 2%, still preferably 1% or less; and a refractive index of 1.45 to 1.70.

If desired, additives such as an infrared absorber and inorganic fine particles may be incorporated into the transparent substrate. The transparent substrate may be subjected to various surface treatments.

Examples of the inorganic fine particles include layered clay minerals, silicon dioxide, titanium dioxide, barium sulfate, and calcium carbonate.

The surface treatments include chemical treatments, mechanical treatments, a corona discharge treatment, a flame treatment, a UV irradiation treatment, a radiofrequency treatment, a glow discharge treatment, an active plasma treatment, a laser treatment, a mixed acid treatment, and an ozone oxidation treatment.

Where a light absorbing layer containing a light absorber is provided, a primer is layer is provided between the transparent substrate and the light absorbing layer. The primer layer is a layer containing a polymer having a glass transition temperature (Tg) of −60 to 60° C., a layer with a rough surface on the light absorbing layer side thereof, or a layer containing a polymer having affinity to the polymer of the light absorbing layer. Even where an independent light absorbing layer is not provided, a primer layer may be provided on the transparent substrate to improve the adhesion between the substrate and a layer provided thereon (e.g., an antireflective layer or a hard coat layer). A primer layer may also be provided in order to improve the affinity of the optical filter to an adhesive with which the optical filter is adhered to an image display device. The thickness of the primer layer is suitably 2 nm to 20 μm, preferably 5 nm to 5 μm, more preferably 20 nm to 2 μm, even more preferably 50 nm to 1 μm, most preferably 80 nm to 300 nm.

The primer layer containing a polymer whose Tg ranges −60 to 60° C. serves to adhere the transparent substrate and a filter layer because of its tackiness. Examples of the polymer whose Tg is −60 to 60° C. include homo- and copolymers of vinyl chloride, vinylidene chloride, vinyl acetate, butadiene, neoprene, styrene, chloroprene, acrylic esters, methacrylic esters, acrylonitrile or methyl vinyl ether. The Tg of the polymer is preferably 50° C. or lower, more preferably 40° C. or lower, even more preferably 30° C. or lower, still even more preferably 25° C. or lower, most preferably 20° C. or lower. It is preferred for the primer layer to have an elastic modulus of 1 to 1000 MPa, more preferably 5 to 800 MPa, even more preferably 10 to 500 MPa, at 25° C.

The primer layer with a rough surface serves for adhesion between the transparent substrate and a light absorbing layer provided on the rough surface side thereof. Such a primer layer can easily be formed by applying a polymer latex. The polymer latex preferably has an average particle size of 0.02 to 3 μm, more preferably 0.05 to 1 μm.

The polymer having affinity to the polymer (binder) of the light absorbing layer includes acrylic resins, cellulose derivatives, gelatin, casein, starch, polyvinyl alcohol, soluble nylon, and polymer latex.

The optical filter may have two or more primer layers. If desired, the primer layer may contain a solvent for swelling a transparent substrate, a matting agent, a surface active agent, an antistatic agent, a coating aid, a hardener, and so forth.

The antireflective layer essentially contains a low refractive sublayer having a lower refractive index than the transparent substrate. The refractive index of the low refractive sublayer is preferably 1.20 to 1.55, still preferably 1.30 to 1.50. The thickness of the low refractive sublayer is preferably 50 to 400 nm, still preferably 50 to 200 nm. The low refractive sublayer may be a layer of low-refractive, fluorine-containing polymer (see JP 57-34526A, JP 3-130103A, JP 6-115023A, JP 8-313702A, and JP 7-168004A), a layer formed by a sol-gel process (see JP 5-208811A, JP 6-299091A, and JP 7-168003A), or a layer containing fine particles (see JP 60-59250B, JP 5-13021A, JP 6-56478A, JP 7-92306A, and JP 9-288201A). The low refractive sublayer containing fine particles may have microvoids formed between the fine particles or inside the fine particles. The low refractive sublayer containing fine particles preferably has a void of 3% to 50% by volume, still preferably 5% to 35% by volume.

In order to prevent reflection over a broad wavelength range, the antireflective layer preferably contains a medium to a high refractive sublayer in addition to the low refractive sublayer. The refractive index of a high refractive sublayer is preferably 1.65 to 2.40, still preferably 1.70 to 2.20. The refractive index of a medium refractive sublayer is set to be the intermediate between the refractive indices of the low and the high refractive sublayers and is preferably 1.50 to 1.90, still preferably 1.55 to 1.70. The thickness of the medium and the high refractive sublayers is preferably 5 nm n to 100 μm, still preferably 10 nm to 10 μm, even still preferably 30 nm to 1 μm. The haze of the medium and the high refractive sublayers is preferably 5% or less, still preferably 3% or less, even still preferably 1% or less. The medium and the high refractive sublayers can be formed by using polymer binders having relatively high refractive indices, such as polystyrene, styrene copolymers, polycarbonates, melamine resins, phenol resins, epoxy resins, and polyurethanes obtained by the reaction between a cyclic (alicyclic or aromatic) isocyanate and a polyol. Polymers having a cyclic (aromatic, heterocyclic or alicyclic) group and polymers having a halogen atom except fluorine as a substituent also have high refractive indices. Polymers prepared from monomers having a double bond introduced therein and thereby capable of radical polymerization are also useful.

Fine inorganic particles may be dispersed in the above recited polymer binders to increase the refractive index. Fine inorganic particles having a refractive index of 1.80 to 2.80 are used preferably. The fine inorganic particles are preferably prepared from metal oxides or sulfides, such as titanium oxide (including rutile, rutile/anatase mixed crystals, anatase, and amorphous oxide), tin oxide, indium oxide, zinc oxide, zirconium oxide, and zinc sulfide. Preferred of them are titanium oxide, tin oxide, and indium oxide. The fine inorganic particles may contain the metal oxide or sulfide as a major component and other elements as a minor component. The term "major component" means a component present in the particles in the highest weight proportion. Other elements that may be present include Ti, Zr, Sn, Sb, Cu, Fe, Mn, Pb, Cd, As, Cr, Hg, Zn, Al, Mg, Si, P, and S. The medium or high refractive sublayer can also be formed by using inorganic materials that are liquid per se or dispersible in a solvent and are capable of forming a film, such as alkoxides of various elements, salts of organic acids, coordination compounds having a coordinating compound bonded (e.g., chelate compounds), and inorganic active polymers.

The surface of the antireflective layer may be endowed with an antiglare function for scattering incident light into all directions thereby preventing the surrounding environment from reflecting on the antireflective layer. For example, fine roughness is formed on a transparent film, and an antireflective layer is formed on the roughened surface, or the surface of an antireflective layer is embossed to have fine surface roughness. An antireflective layer with an antiglare function usually has a haze of 3% to 30%.

The hard coat layer has higher hardness than the transparent substrate. The hard coat layer preferably contains a crosslinked polymer. The hard coat layer can be formed by using polymers, oligomers or monomers of acryl, urethane or epoxy, such as UV curing resins. The hard coat layer can also be made of a silica-based material.

A lubricating layer may be provided on the antireflective layer (low refractive sublayer). A lubricating layer imparts slip properties to the surface of the low refractive sublayer thereby improving scratch resistance. The lubricating layer can be formed using organopolysiloxanes (e.g., silicone oil), natural waxes, petroleum waxes, higher fatty acid metal salts, or fluorine-containing lubricants or derivatives thereof. The lubricating layer preferably has a thickness of 2 to 20 nm.

Where a light absorbing layer is provided independent of the above described layers, the light absorbing layer can be formed of the indole compound of the invention either alone or in combination with a binder. Examples of useful binders include naturally occurring polymers, such as gelatin, casein, starch, cellulose derivatives, and alginic acid, and synthetic polymers, such as polymethyl methacrylate, polyvinyl butyral, polyvinylpyrrolidone, polyvinyl alcohol, polyvinyl chloride, styrene-butadiene copolymers, polystyrene, polycarbonate, polyamide, polyurethane, polyester, and polyurea.

The primer layer, antireflective layer, hard coat layer, lubricating layer, light absorbing layer, and the like can be formed by commonly employed coating methods including dip coating, air knife coating, curtain coating, roller coating, wire bar coating, gravure coating, and extrusion coating using a hopper (see U.S. Pat. No. 2,681,294). Two or more layers can be formed by simultaneous coating. For the details of simultaneous coating techniques, reference can be made in U.S. Pat. Nos. 2,761,791, 2,941,898, 3,508,947, and 3,526,528, and Harasaki Yuji, Coating Kogaku, Asakura Shoten, 1973, p. 253.

The optical recording material of the present invention, which contains the indole compound of the invention, will then be described.

The optical recording material of the invention is used to form an optical recording layer of an optical recording medium. It is applicable to a variety of optical recording media in accordance with the absorption characteristics of the indole compound used. Of the optical recording materials of the invention, particularly suited to optical disks for short wavelength lasers (380 to 420 nm) are those containing an indole compound the absorption characteristics of which are such that the maximum absorption wavelength $\lambda_{max}$ is in the range of from 320 to 420 nm in the form of a solution. The absorption intensity $\epsilon$ at $\lambda_{max}$ is preferably $1.0 \times 10^4$ or more. If the absorption intensity $\epsilon$ is less than that, the recording sensitivity tends to be reduced. Measurements of $\lambda_{max}$ and $\epsilon$ of a solution of the indole compound are made in a usual manner using a selected solvent at a selected concentration.

The method of forming an optical recording layer to provide an optical recording medium using the indole compound-containing optical recording material of the present invention is not particularly limited. Generally followed methods include wet coating processes, wherein a solution of the indole compound is coated on a substrate, such as spin coating, spraying and dipping, or dry coating processes such as vacuum evaporation and sputtering. The solution to be used in wet coating processes is prepared by dissolving the indole compound and, if desired, other compounds in an organic solvent. Suitable organic solvents include lower alcohols, such as methanol and ethanol; ether alcohols, such as methyl cellosolve, ethyl cellosolve, butyl cellosolve, and butyl diglycol; ketones, such as acetone, methyl ethyl ketone, methyl isobutyl ketone, cyclohexanone, and diacetone alcohol; esters, such as ethyl acetate, butyl acetate, and methoxyethyl acetate; acrylic esters, such as ethyl acrylate and butyl acrylate; fluoroalcohols, such as 2,2,3,3-tetrafluoropropanol; hydrocarbons, such as benzene, toluene, and xylene; and chlorinated hydrocarbons, such as methylene dichloride, dichloroethane, and chloroform.

The optical recording layer is formed as a thin film usually with a thickness of 0.001 to 10 μm, preferably 0.01 to 5 μm.

The content of the indole compound in the optical recording material is preferably 10% to 100% by mass on a solid basis. The optical recording layer preferably contains 50% to 100% by mass of the indole compound of general formula (I). In order to form an optical recording layer having the recited preferred indole compound content, it is still preferred for the optical recording material of the invention to contain 50% to 100% by mass of the indole compound of general formula (I) on a solid basis.

If desired, the optical recording material of the invention can contain compounds commonly employed in an optical recording layer, such as cyanine compounds, azo compounds, phthalocyanine compounds, oxonol compounds, squarylium compounds, styryl compounds, porphyrin compounds, azulenium compounds, croconic methine compounds, pyrylium compounds, thiopyrylium compounds, triarylmethane compounds, diphenylmethane compounds, tetrahydrocholine compounds, indophenol compounds, anthraquinone compounds, naphthoquinone compounds, xanthene compounds, thiazine compounds, acridine compounds, oxazine compounds, spiropyran compounds, fluorene compounds, and rhodamine compounds. The optical recording material can further contain resins, such as polyethylene, polyester, polystyrene, and polycarbonate, surface active agents, antistatic agents, lubricants, flame retardants, radical scavengers (e.g., hindered amines), pit formation accelerators (e.g., ferrocene derivatives), dispersants, antioxidants, crosslinking agents, light resistance imparting agents, and so forth. The optical recording material can furthermore contain an aromatic nitroso compound, an aminium compound, an iminium compound, a bisiminium compound, a transition metal chelate compound, and the like as a quencher, e.g., for singlet oxygen. For the same purpose, a quencher anion may be used. The total content of these various compounds in the optical recording material is preferably up to 50% by mass on a solid basis.

The substrate on which the optical recording layer is provided is not particularly limited in material as long as it is substantially transparent to a write/read (recording/reproducing) light beam and includes resins, such as polymethyl methacrylate, polyethylene terephthalate, and polycarbonate, and glass. The substrate can have any shape, including a tape, a drum, a belt, and a disk.

A reflective layer of gold, silver, aluminum, copper, etc. may be formed on the optical recording layer by vacuum evaporation or sputtering. A protective layer of an acrylic resin, a UV cured resin, etc. may be provided on the optical recording layer.

EXAMPLES

The present invention will now be illustrated in greater detail with reference to Examples and Comparative Examples, but it should be understood that the invention is not construed as being limited thereto.

Example 1

Synthesis of Compound No. 1

In a nitrogen-purged reaction flask were put 10 ml of dimethylformamide (DMF) and 80 ml of chloroform, and 6.91 g (45.1 mmol) of phosphorus oxychloride was added thereto dropwise under ice cooling, followed by stirring for 1 hour under ice cooling. A solution of 3.94 g (30.0 mmol) of 1-methylindole in 40 ml of chloroform was added thereto dropwise while cooling with ice, followed by heating under reflux for 3 hours. The reaction mixture was cooled to room temperature and slowly dropped into a 400 ml aqueous solution of 23.1 g (126 mmol) of potassium hexafluorophosphate, followed by stirring at room temperature for 2 hours. The precipitate thus formed was collected by filtration, washed by stirring in 200 ml of methanol at room temperature for 30 minutes, and filtered. The filer cake was dried to give 9.32 g (yield: 93.4%) of a pink solid, which was identified to be compound No. 1. The analysis results of the resulting compound are shown below.

(1) $^1$H-NMR (ppm, DMSO Solvent)

3.57 (s, 3H), 3.74 (s, 3H), 4.01 (s, 3H), 7.39-7.50 (m, 2H), 7.26-7.65 (m, 1H), 8.00-8.10 (m, 1H), 8.70 (s, 1H), 9.12 (s, 1H)

(2) IR Absorption ($cm^{-1}$)

3168, 1647, 1536, 1466, 1402, 1349, 1256, 1113, 838, 758

(3) UV Absorption (Acetone Solvent)

$\lambda_{max}$: 345.0 nm; $\epsilon$: 1.86×10$^4$ (concentration 6.68×10$^{-6}$ mol/l)

(4) Decomposition Temperature (TG-DTA; 100 ml/min Nitrogen Stream; Temperature Rise: 10° C./min)

Melting point: 295.8° C.; mass loss initiation temperature: 326.7° C.

Example 2

Synthesis of Compound No. 2

In a nitrogen-purged reaction flask were put 10 ml of DMF and 80 ml of chloroform, and 6.90 g (45.0 mmol) of phosphorus oxychloride was added thereto dropwise under ice cooling, followed by stirring for 1 hour under ice cooling. A solution of 6.22 g (30.0 mmol) of 1-methyl-2-phenylindole in 40 ml of chloroform was added thereto dropwise while cooling with ice, followed by heating under reflux for 3 hours. The reaction mixture was cooled to room temperature and slowly dropped into a 400 ml aqueous solution of 20.0 g (109 mmol) of potassium hexafluorophosphate, followed by stirring at room temperature for 30 minutes. The aqueous layer was discarded. To the organic layer was added 400 ml of water, followed by stirring at room temperature for 30 minutes. The precipitate thus formed was collected by filtration, washed by stirring in 150 ml of methanol at room temperature for 30 minutes, and filtered. The filer cake was dried to give a grayish white solid. Recrystallization from an acetonitrile/ethanol mixed solvent gave 5.06 g (yield: 41.5%) of a grayish white solid, which was identified to be compound No. 2. The analysis results of the resulting compound are shown below.

(1) $^1$H-NMR (ppm, DMSO Solvent)

3.53 (s, 3H), 3.68 (s, 3H), 3.82 (s, 3H), 7.45-7.55 (m, 2H), 7.58-7.75 (m, 5H), 7.83 (d, 1H, J=7.8 Hz), 7.88 (d, 1H. J=7.6 Hz), 8.51 (s, 1H)

(2) IR Absorption ($cm^{-1}$)

3430, 1656, 1490, 1474, 1463, 1391, 1120, 842, 795, 754, 705

(3) UV Absorption (Acetone Solvent)

$\lambda_{max}$: 348.5 nm; $\epsilon$: 1.74×10$^4$ (concentration 1.93×10$^6$ mol/l)

(4) Decomposition Temperature (TG-DTA; 100 ml/min Nitrogen Stream; Temperature rise: 10° C./min)

Melting point: 162.6° C.; mass loss initiation temperature: 332.9° C.

Example 3

Synthesis of Compound No. 3

In a nitrogen-purged reaction flask were put 15 g (95.4 mmol) of N,N-n-dibutylformamide and 5.21 g (34.0 mmol) of phosphorus oxychloride under ice cooling, followed by stirring for 1 hour under ice cooling. To the mixture was added 2.62 g (20.0 mmol) of 1-methylindole under ice cooling, followed by stirring at 100° C. for 3 hours. The reaction mixture was cooled to room temperature, and N,N-n-dibutylformamide was removed by evaporation. Into the residue was uniformly mixed 15.3 g (95.4 mmol) of potassium hexafluorophosphate, and 150 ml of water was added thereto, followed by stirring at room temperature for 30 minutes. The precipitate thus formed was collected by filtration, washed by addition of 100 ml of methanol, followed by stirring at room temperature for 30 minutes and addition of 50 ml of water, followed by stirring at room temperature for 30 minutes. The solid was collected by filtration and dried to give an ocher solid. The solid was recrystallized from an acetonitrile/methanol mixed solvent, filtered, and dried to furnish 2.90 g (yield: 34.8%) of a faint pink solid, which was identified to be the compound No. 3. The analytical results of compound No. 3 are shown below.

(1) $^1$H-NMR (ppm, DMSO Solvent)

0.96 (t, 3H, J=7.3 Hz), 0.97 (t, 3H, J=7.3 Hz), 1.36 (tq, 2H, J=7.6, 7.3 Hz), 1.52 (tq, 2H, J=7.8, 7.6 Hz), 1.70-1.89 (m, 4H), 3.85-3.99 (m, 4H), 4.05 (s, 3H), 7.45 (dd, 1H, J=6.6, 3.9 Hz), 7.46 (dd, 1H, J=6.6, 3.7 Hz), 7.68-7.80 (m, 1H), 8.08-8.20 (m, 1H), 8.56 (s, 1H), 9.08 (s, 1H)

(2) IR Absorption ($cm^{-1}$)

2955, 2874, 1639, 1532, 1476, 1352, 1256, 1114, 834, 751

(3) UV Absorption (Chloroform Solvent)

$\lambda_{max}$: 357.0 nm; $\epsilon$: 2.04×10$^4$ (concentration 5.64×10$^{-6}$ mol/l)

(4) Decomposition Temperature (TG-DTA; 100 ml/min Nitrogen Stream; Temperature Rise: 10° C./min)

Melting point: 179.7° C.; mass loss initiation temperature: 307.8° C.

Example 4

Synthesis of Compound No. 4

In a nitrogen-purged reaction flask were put 15 g (95.4 mmol) of N,N-n-dibutylformamide and 5.21 g (34.0 mmol) of phosphorus oxychloride under ice cooling, followed by stirring for 1 hour under ice cooling. To the mixture was added 6.22 g (30.0 mmol) of 1-methylindole under ice cooling, followed by stirring at 100° C. for 4 hours. The reaction mixture was cooled to room temperature, and N,N-n-dibutylformamide was removed by evaporation. Into the residue was uniformly mixed 25.0 g (132 mmol) of potassium trifluoromethanesulfonate, and 150 ml of water was added thereto, followed by ultrasonication at room temperature for 30 minutes. The precipitate thus formed was collected by filtration, recrystallized from an ethanol/diethyl ether mixed solvent, filtered, and dried to give 4.64 g (yield: 55.1%) of a faint yellow solid, which was identified to be the compound No. 4. The analytical results of compound No. 4 are shown below.

(1) $^1$H-NMR (ppm, DMSO Solvent)

0.94 (t, 3H, J=6.6 Hz), 0.96 (t, 3H, J=7.1 Hz), 1.35 (tq, 2H, J=7.6, 7.6 Hz), 1.51 (tq, 2H, J=7.6, 7.6 Hz), 1.70-1.85 (m, 4H), 3.85-3.95 (m, 4H), 4.05 (s, 3H), 7.35-7.50 (m, 2H), 7.65-7.80 (m, 1H), 8.05-8.20 (m, 1H), 8.58 (s, 1H), 9.09 (s, 1H)

(2) IR Absorption (cm$^{-1}$)

2960, 2874, 1624, 1588, 1476, 1464, 1430, 1265, 1153, 1032, 965

(3) UV Absorption (Chloroform Solvent)

$\lambda_{max}$: 356.5 nm; $\epsilon$: 1.84×10$^4$ (concentration 9.89×10$^{-6}$ mol/l)

(4) Decomposition Temperature (TG-DTA; 100 ml/min Nitrogen Stream; Temperature rise: 10° C./min)

Melting point: 110.3° C.; mass loss initiation temperature: 287.1° C.

Example 5

Synthesis of Compound No. 5

In a nitrogen-purged reaction flask were put 22.5 g (143 mmol) of N,N-n-dibutylformamide and 7.82 g (51.0 mmol) of phosphorus oxychloride under ice cooling, followed by stirring for 1 hour under ice cooling. To the mixture was added 6.08 g (18.4 mmol) of 1-(3,5-bistrifluoromethylphenyl)indole under ice cooling, followed by stirring at 100° C. for 4 hours. The reaction mixture was cooled to room temperature, and N,N-n-dibutylformamide was removed by evaporation. Into the residue was uniformly mixed 50.0 g (272 mmol) of potassium hexafluorophosphate, and 1 liter of water was added thereto, followed by stirring at room temperature for 30 minutes. The aqueous layer was discarded, and the organic layer was washed by stirring in 1 liter of ethanol for 30 minutes. The precipitate was collected by filtration, recrystallized from an acetone/ethanol mixed solvent, filtered, and dried to afford 2.75 g (yield: 24.3%) of colorless needle-like crystals, which were identified to be compound No. 5. The analytical results of compound No. 5 are shown below.

(1) $^1$H-NMR (ppm, DMSO Solvent)

0.96 (t, 3H, J=7.6 Hz), 0.99 (t, 3H, J=7.1 Hz), 1.40 (tq, 2H, J=7.3, 7.1 Hz), 1.48 (tq, 2H, J=7.6, 7.6 Hz), 1.78-1.95 (m, 4H), 4.05 (t, 2H, J=7.6 Hz), 4.11 (t, 2H, J=7.8 Hz), 7.51 (dd, 1H, J=8.5, 7.1 Hz), 7.55 (dd, 1H, J=7.8, 7.1 Hz), 7.64 (d, 1H, J=8.3 Hz), 8.26 (d, 1H, J=7.6 Hz), 8.41 (s, 1H), 8.60 (s, 2H), 8.83 (s, 1H), 9.34 (s, 1H)

(2) IR Absorption (cm$^{-1}$)

2967, 2880, 1646, 1522, 1475, 1360, 1282, 1230, 1192, 1146, 843, 825, 762

(3) UV Absorption (Chloroform Solvent)

$\lambda_{max}$: 354.5 nm; $\epsilon$: 1.92×10$^4$ (concentration 6.87×10$^{-6}$ mol/l)

(4) Decomposition Temperature (TG-DTA; 100 ml/min Nitrogen Stream; Temperature Rise: 10° C./min)

Melting point: 183.3° C.; mass loss initiation temperature: 297.5° C.

Example 6

Synthesis of Compound No. 6

In a nitrogen-purged reaction flask were put 22.5 g (143 mmol) of N,N-n-dibutylformamide and 7.82 g (51.0 mmol) of phosphorus oxychloride under ice cooling, followed by stirring for 1 hour under ice cooling. To the mixture was added 6.22 g (30.0 mmol) of 1-methyl-2-phenylindole under ice cooling, followed by stirring at 10° C. for 4 hours. The reaction mixture was cooled to room temperature, and N,N-n-dibutylformamide was removed by evaporation. Into the residue was uniformly mixed 50.0 g (272 mmol) of potassium hexafluorophosphate, and 1 liter of water was added thereto, followed by stirring at room temperature for 30 minutes for washing. The precipitate was collected by filtration, recrystallized from an acetone/ethanol mixed solvent, filtered, and dried to afford 3.02 g (yield: 20.4%) of a pale green solid, which is was identified to be the compound No. 6. The analytical results of compound No. 6 are shown below.

(1) $^1$H-NMR (ppm, DMSO Solvent)

0.80 (t, 3H, J=7.3 Hz), 0.90 (t, 3H, J=7.3 Hz), 1.20 (tq, 2H, J=7.6, 7.6 Hz), 1.30 (tq, 2H, J=7.6, 7.6 Hz), 1.65-1.79 (m, 4H), 3.82 (s, 3H), 3.89 (t, 2H, J=6.8 Hz), 3.91 (t, 2H, J=6.8 Hz), 7.49 (dd, 1H, J=7.2, 7.2 Hz), 7.53 (dd, 1H, J=7.1, 7.1 Hz), 7.57-7.63 (m, 2H), 7.64-7.77 (m, 3H), 7.80 (d, 1H, J=7.8 Hz), 7.85 (d, 1H, J=7.8 Hz), 8.54 (s, 1H)

(2) IR Absorption (cm$^{-1}$)

2960, 2935, 2874, 1651, 1477, 1464, 1404, 1368, 1086, 838, 802, 750

(3) UV Absorption (Chloroform Solvent)

$\lambda_{max}$: 352.5 nm; $\epsilon$: 2.48×10$^4$ (concentration 4.07×10$^{-6}$ mol/l)

(4) Decomposition Temperature (TG-DTA; 100 ml/min Nitrogen Stream; Temperature rise: 10° C./min)

Melting point: 100.4° C.; mass loss initiation temperature: 304.9° C.

Example 7

Synthesis of Compound No. 21

In a nitrogen-purged reaction flask were put 10 ml of N,N-n-dimethylformamide, 80 ml of chloroform, and 6.74 g (44.0 mmol) of phosphorous oxychloride while cooling with ice, and the mixture was stirred for 1 hour under ice cooling. A solution of 10.5 g (29.3 mmol) of 1-propylferrocenylindole in 40 ml of chloroform was added thereto while cooling with ice, followed by heat under reflux for 3.5 hours. After cooling to room temperature, the reaction mixture was slowly added dropwise to a solution of 23.5 g (127 mmol) of potassium hexafluorophosphate in 500 ml of water, followed by stirring at room temperature for 1 hour. The precipitate thus formed was collected by filtration and dried to famish 16.2 g (yield: 99.4%) of a brown solid, which was identified to be compound No. 21. The analytical results of compound No. 21 are shown below.

(1) $^1$H-NMR (ppm, DMSO Solvent)

1.48 (dt, 2H, J=7.3, 7.3 Hz), 1.90 (dt, 2H, J=7.3, 7.3 Hz), 2.32 (t, 2H, J=7.6 Hz), 3.61 (s, 3H), 3.74 (s, 3H), 4.03 (s, 5H), 3.98-4.05 (m, 4H), 4.44 (t, 2H, J=7.3 Hz), 7.35-7.50 (m, 2H), 7.81 (d, 1H, J=7.1 Hz), 8.08 (d, 1H, J=6.8 Hz), 8.76 (s, 1H), 9.17 (s, 1H)

(2) IR Absorption (cm$^{-1}$)

1654, 1530, 1404, 1364, 1105, 836

(3) UV Absorption (Chloroform Solvent)

$\lambda_{max}$: 353.0 nm; $\epsilon$: 2.10×10$^4$ (concentration 1.59×10$^{-5}$ mol/l)

(4) Decomposition Temperature (TG-DTA; 100 ml/min Nitrogen Stream; Temperature Rise: 10° C./min)

Melting point: 200.5° C.; mass loss initiation temperature: 284.7° C.

Example 8

Synthesis of Compound No. 24

In a nitrogen-purged reaction flask were put 43.6 g (277 mmol) of N,N-n-dibutylformamide and 13.3 g (87.1 mmol) of phosphorus oxychloride while cooling with ice, followed by stirring for 1 hour under ice cooling. To the mixture was added 12.2 g (58.0 mmol) of 5-bromo-1-methylindole under ice cooling, followed by stirring at 100° C. for 4 hours. The reaction mixture was cooled to room temperature, and N,N-n-dibutylformamide was removed by evaporation. Into the residue was uniformly mixed 58.0 g (315 mmol) of potassium hexafluorophosphate, and 1 liter of water was added thereto, followed by stirring at room temperature for 30 minutes for washing. The precipitate was collected by filtration, recrystallized from an acetone/methanol mixed solvent, filtered, and dried to give 18.9 g (yield: 65.8%) of a pale yellow solid, which was identified to be compound No. 24. The analytical results of compound No. 24 are shown below.

(1) $^1$H-NMR (ppm, DMSO Solvent)

0.95 (t, 3H, J=7.3 Hz), 0.96 (t, 3H, J=7.3 Hz), 1.36 (tq, 2H, J=7.3, 7.8 Hz), 1.50 (tq, 2H, J=7.6, 7.8 Hz), 1.72-1.87 (m, 4H), 3.91 (t, 4H, J=7.1 Hz), 4.04 (s, 3H), 7.59 (dd, 1H, J=1.7, 8.8 Hz), 7.71 (d, 1H, J=8.8 Hz), 8.41 (d, 1H, J=1.7 Hz), 8.58 (s, 1H), 9.11 (s, 1H)

(2) IR Absorption ($cm^{-1}$)

2964, 1638, 1530, 1449, 1353, 1253, 1123, 838

(3) UV Absorption (Chloroform Solvent)

$\lambda_{max}$: 354.0 nm; $\epsilon$: 2.14×10$^4$ (concentration 1.01×10$^{-5}$ mol/l)

(4) Decomposition Temperature (TG-DTA; 100 ml/min Nitrogen Stream; Temperature Rise: 10° C./min)

Melting point: 161.7° C.; mass loss initiation temperature: 313.8° C.

Example 9

Synthesis of Compound No. 23

In 20 ml of acetone was dissolved 2.06 g (4.18 mmol) of compound No. 24 prepared in Example 8, and a solution of 5.0 mmol of a triethylamine salt of the anion represented by chemical formula (C) in 162 ml of acetone was added thereto dropwise, followed by heating under reflux for 3 hours. After cooling to room temperature, the reaction mixture was slowly added dropwise to 800 ml of water, followed by stirring at room temperature for 14 hours. The precipitate thus formed was collected by filtration, washed with acetone, and dried to give 4.18 g (yield: 93.7%) of a reddish brown solid, which was identified to be compound No. 23. The analysis results of compound No. 23 are shown below.

(1) $^1$H-NMR (ppm, DMSO Solvent)

0.95 (t, 6H, J=7.1 Hz), 1.01 (t, 12H, J=7.1 Hz), 1.36 (tq, 2H, J=7.3, 7.3 Hz), 1.48 (tq, 2H, J=7.3, 7.3 Hz), 1.72-1.85 (m, 4H), 3.29 (q, 8H, J=6.8 Hz), 3.89 (t, 4H, J=7.6 Hz), 4.00 (s, 3H), 5.74 (d, 2H, J=2.4 Hz), 6.35 (dd, 2H, J=2.7, 9.5 Hz), 6.55 (d, 2H, J=9.3 Hz), 7.58 (dd, 1H, J=1.7, 8.8 Hz), 7.64 (d, 2H, J=9.3 Hz), 7.69 (d, 1H, J=8.8 Hz), 7.84 (dd, 2H, J=2.9, 9.3 Hz), 8.39 (d, 1H, J=1.7 Hz), 8.54 (s, 1H), 9.00 (d, 2H, J=2.9 Hz), 9.08 (s, 1H)

(2) IR Absorption ($cm^{-1}$)

2975, 1611, 1578, 1459, 1320, 1283, 1262, 1141

(3) UV Absorption (Chloroform Solvent)

$\lambda_{max}$: 357.5 nm; $\epsilon$: 3.95×10$^4$ 541.5 nm; $\epsilon$: 6.20×10$^4$ (concentration 2.18×10$^{-6}$ mol/l)

(4) Decomposition Temperature (TG-DTA; 100 ml/min Nitrogen Stream; Temperature Rise: 10° C./min)

Melting point: 216.8° C.; mass loss initiation temperature: 258.9° C.

Example 10

Preparation of Optical Filter Having Adhesive Layer

A UV varnish prepared according to the following formulation was applied, with a bar coater #9, to a 188 μm thick PET film having been subjected to an adhesion enhancing treatment and dried at 100° C. for 10 minutes. The coating film was irradiated with 100 mJ UV light from a high pressure mercury lamp equipped with an IR cut filter to obtain an optical filter composed of the PET film and a cured film (pressure-sensitive adhesive layer) having a thickness of about 5 μm. The optical filter had a $\lambda_{max}$ of 353 nm as measured with a UV-visible-near IR spectrophotometer V-570 (from JASCO Corp.).

Formulation:

| | |
|---|---|
| Compound No. 4 | 2.0 mg |
| Acrylic pressure-sensitive adhesive DB5541 (from Diabond Ind. Co., Ltd.) | 20 g |
| Methyl ethyl ketone | 80 g |

Example 11

Preparation of Optical Filter

A UV varnish prepared according to the following formulation was applied, with a bar coater #9, to a 188 μm thick PET film having been subjected to an adhesion enhancing treatment and dried at 100° C. for 10 minutes. The coating film was irradiated with 100 mJ UV light from a high pressure mercury lamp equipped with an IR cut filter to obtain an optical filter composed of the PET film and a cured film having a thickness of about 5 μm. The optical filter had a $\lambda_{max}$ of 354 nm as measured with a UV-visible-near IR spectrophotometer V-570 (from JASCO Corp.).

Formulation:

| | |
|---|---|
| UV-curing resin Adecaoptomer KRX-571-65 (resin content: 80 wt %; from ADEKA Corp.) | 100 g |
| Compound No. 5 | 2.0 mg |
| Methyl ethyl ketone | 60 g |

Example 12

Preparation of Optical Recording Material and Optical Recording Medium and Evaluation of Optical Recording Medium Compound No. 4 obtained in Example 4 was dissolved in 2,2,3,3-tetrafluoropropanol in a concentration of 1.0% by mass to prepare a solution as an optical recording material.

A titanium chelate compound T-50 (from Nippon Soda Co., Ltd.) was applied to a 12 cm diameter polycarbonate disk substrate and hydrolyzed to form a 0.01 μm thick primer layer. The above prepared optical recording material was applied thereon by spin coating to form a 100 nm thick optical recording layer thereby to obtain an optical recording medium. The thin film of the resulting optical recording medium was measured for absorption UV spectrum and reflection UV spectrum (incidence angle: 5°). As a result, the absorption $\lambda_{max}$ was 353 nm, and the reflected light $\lambda_{max}$ was 382 nm.

The filters containing the indole compound of the invention have an absorption maximum in a specific wavelength range (340 to 390 nm) (see Examples 10 and 11). The indole compounds are thus proved suitable as a UV absorber for optical filters.

The optical recording medium having an optical recording layer formed of the indole compound-containing optical recording material according to the invention has a reflected light absorption maximum in a specific wavelength range (340 to 390 nm) (see Example 12). In reading an optical recording medium typified by an optical disk, a laser beam reflected from the medium is received to detect the presence or absence of recorded information from the difference in reflected light quantity. It is hence preferred for an optical recording medium to show a large absorption intensity at near the wavelength of a laser beam used in the reflection spectrum. Therefore, the indole compound-containing optical recording material of the present invention is suited as a material forming an optical recording layer of an optical recording medium using a laser beam of 405 nm, such as an optical disk for a short wavelength laser.

Evaluation Examples 1-1 to 1-5 and Comparative Evaluation Example 1-1

Evaluation of Light Resistance of Compound Represented by General Formula (I)

Compound Nos. 21, 23, and 24 obtained in Examples 7 to 9 and Comparative Compound No. 1 were evaluated for light resistance as follows.

Each of the compounds was dissolved in 2,2,3,3-tetrafluoropropanol to prepare a 1% by mass solution. The solution was applied to a 20 mm by 20 mm polycarbonate plate by spin coating at 2000 rpm for 60 seconds to prepare a specimen. The specimen was irradiated with 55000 lux light for 24 hours and 150 hours. The UV absorption spectra measured before and after the irradiation were compared to calculate an absorbance retention at the $\lambda_{max}$ of the UV absorption spectrum before the irradiation. The results obtained are shown in Table 1 below. In Evaluation Examples 1-4 and 1-5, the diimmonium compound or dithiol compound shown below was used in combination as dissolved in the 2,2,3,3-tetrafluoropropanol solvent in a concentration of 0.1% by mass.

TABLE 1

| | | Absorbance Retention (%) | |
|---|---|---|---|
| | Test Compound | After 24 hrs | After 150 hrs |
| Evaluation Example 1-1 | compound No. 21 | 95.8 | 89.9 |
| Evaluation Example 1-2 | compound No. 23 | 97.2 | 91.6 |
| Evaluation Example 1-3 | compound No. 24 | 25.9 | 25.0 |
| Evaluation Example 1-4 | compound No. 24 dithiol compound | 95.5 | 21.0 |
| Evaluation Example 1-5 | compound No. 24 diimmonium compound | 92.2 | 3.9 |

TABLE 1-continued

| | | Absorbance Retention (%) | |
|---|---|---|---|
| | Test Compound | After 24 hrs | After 150 hrs |
| Compara. Evaluation Example 1-1 | comparative compound No. 1 | 1.7 | 0 |

[Chemical Formula 9]

Comparative Compound No. 1

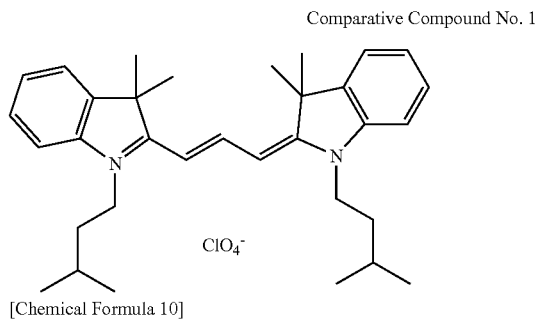

[Chemical Formula 10]

Dimmonium Compound

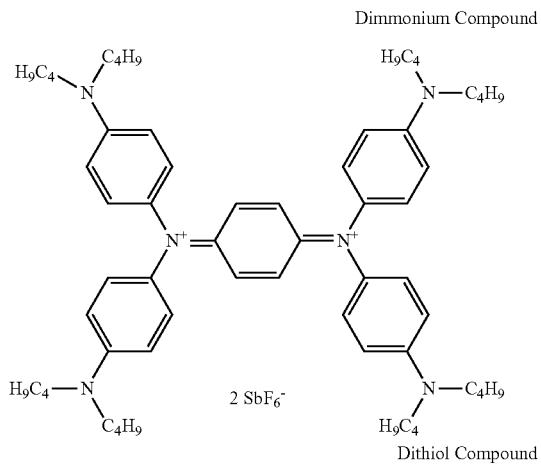

Dithiol Compound

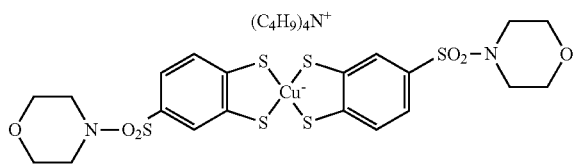

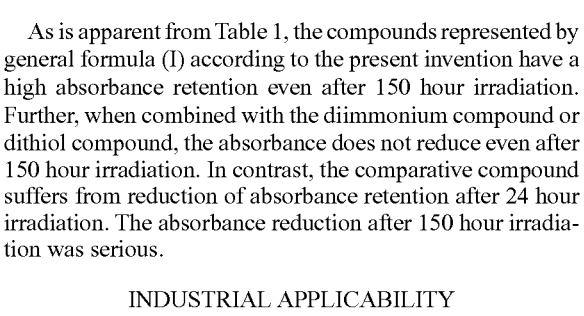

As is apparent from Table 1, the compounds represented by general formula (I) according to the present invention have a high absorbance retention even after 150 hour irradiation. Further, when combined with the diimmonium compound or dithiol compound, the absorbance does not reduce even after 150 hour irradiation. In contrast, the comparative compound suffers from reduction of absorbance retention after 24 hour irradiation. The absorbance reduction after 150 hour irradiation was serious.

INDUSTRIAL APPLICABILITY

The present invention provides a novel indole compound suitable as an optical element. An optical filter using the indole compound is fit for use as an optical filter for image displays, and an optical recording material containing the indole compound is suited for the formation of an optical recording layer to provide an optical recording medium.

The invention claimed is:

1. An optical filter containing an indole compound represented by general formula (I):

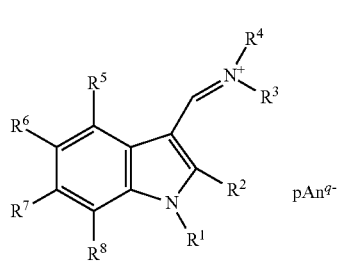

(I)

wherein,
$R^1$ and $R^2$ each represent a hydrogen atom, a hydrocarbon group having 1 to 30 carbon atoms or a substituent represented by general formula (II) below;
$R^3$ and $R^4$ each represent an alkyl group having 1 to 10 carbon atoms, an alkoxy group having 1 to 10 carbon atoms or an aryl group having 6 to 30 carbon atoms;
$R^5$, $R^6$, $R^7$, and $R^8$ each represent a hydrogen atom, a hydrocarbon group having 1 to 30 carbon atoms, a halogen atom, a hydroxyl group, a nitro group, a cyano group, NHR or NR'R";
R, R', and R" each represent an alkyl group having 1 to 10 carbon atoms, or R' and R" are taken together to form a ring;
$R^5$ and $R^6$, $R^6$ and $R^7$, or $R^7$ and $R^8$ may be taken together to form a ring; $An^{q-}$ represents a q-valent anion;
q represents 1 or 2; and
p represents a coefficient necessary to maintain charge neutrality,

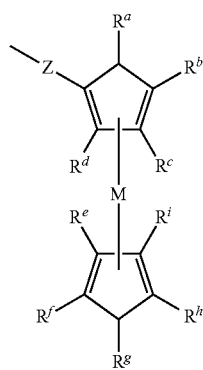

(II)

wherein,
$R^a$, $R^b$, $R^c$, $R^d$, $R^e$, $R^f$, $R^g$, $R^h$, and $R^i$ each represent a hydrogen atom or an alkyl group having 1 to 4 carbon atoms, and a methylene group of the alkyl group may be replaced by —O— or —CO—;
Z represents a single bond or a substituted or unsubstituted alkylene group having 1 to 8 carbon atoms, and a methylene group of the alkylene group may be replaced by —O—, —S—, —CO—, —COO—, —OCO—, —SO$_2$—, —NH—, —CONH—, —NHCO—, —N=CH— or —CH=CH—; and
M represents a metal atom.

2. The optical filter as set forth in claim 1, which is applied to an image display device.

3. An optical recording medium comprising a substrate and an optical recording layer on the substrate, wherein the optical recording layer is formed from an optical recording material comprising an indole compound represented by general formula (I):

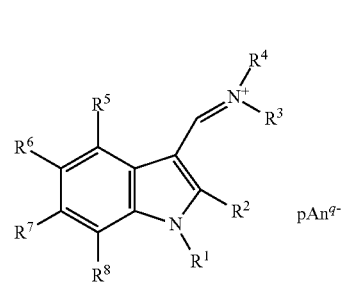

(I)

wherein,
$R^1$ and $R^2$ each represent a hydrogen atom, a hydrocarbon group having 1 to 30 carbon atoms or a substituent represented by general formula (II) below;
$R^3$ and $R^4$ each represent an alkyl group having 1 to 10 carbon atoms, an alkoxy group having 1 to 10 carbon atoms or an aryl group having 6 to 30 carbon atoms;
$R^5$, $R^6$, $R^7$, and $R^8$ each represent a hydrogen atom, a hydrocarbon group having 1 to 30 carbon atoms, a halogen atom, a hydroxyl group, a nitro group, a cyano group, NHR or NR'R";
R, R', and R" each represent an alkyl group having 1 to 10 carbon atoms, or R' and R" are taken together to form a ring;
$R^5$ and $R^6$, $R^6$ and $R^7$, or $R^7$ and $R^8$ may be taken together to form a ring;
$An^{q-}$ represents a q-valent anion;
q represents 1 or 2; and
p represents a coefficient necessary to maintain charge neutrality,

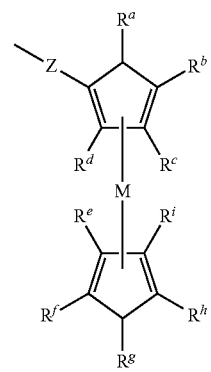

(II)

wherein,
$R^a$, $R^b$, $R^c$, $R^d$, $R^e$, $R^f$, $R^g$, $R^h$, and $R^i$ each represent a hydrogen atom or an alkyl group having 1 to 4 carbon atoms, and a methylene group of the alkyl group may be replaced by —O— or —CO—;
Z represents a single bond or a substituted or unsubstituted alkylene group having 1 to 8 carbon atoms, and a methylene group of the alkylene group may be replaced by —O—, —S—, —CO—, —COO—, —OCO—, —SO$_2$—, —NH—, —CONH—, —NHCO—, —N═CH— or —CH═CH—; and M represents a metal atom.

4. The optical filter as set forth in claim 1, wherein, in the above general formula (I), R$^1$ is a hydrocarbon group having 1 to 30 carbon atoms;
R$^2$ is a hydrogen atom or a hydrocarbon group having 1 to 30 carbon atoms;
R$^3$ is an alkyl group having 1 to 10 carbon atoms; and
R$^4$ is an alkyl group having 1 to 10 carbon atoms.

5. The optical filter as set forth in claim 2, wherein, in the above general formula (I), R$^1$ is a hydrocarbon group having 1 to 30 carbon atoms;
R$^2$ is a hydrogen atom or a hydrocarbon group having 1 to 30 carbon atoms;
R$^3$ is an alkyl group having 1 to 10 carbon atoms; and
R$^4$ is an alkyl group having 1 to 10 carbon atoms.

* * * * *